United States Patent [19]

Takezono et al.

[11] Patent Number: 4,645,576
[45] Date of Patent: Feb. 24, 1987

[54] PROCESS FOR ISOLATING AND RECOVERING BUTENE-1 OF HIGH PURITY

[75] Inventors: Tetsuya Takezono, Kawasaki; Takaaki Amari; Hirosuke Imai, both of Yokohama, all of Japan

[73] Assignee: Nippon Oil Co., Ltd., Tokyo, Japan

[21] Appl. No.: 608,746

[22] Filed: May 10, 1984

[30] Foreign Application Priority Data

May 17, 1983 [JP] Japan ................................. 58-85018

[51] Int. Cl.$^4$ ............................................. B01D 3/34
[52] U.S. Cl. ...................................... 203/30; 203/73; 203/DIG. 6; 585/811; 585/829; 585/832; 585/833
[58] Field of Search ...................... 203/28, DIG. 6, 29, 203/71, 73, 38, DIG. 18, 80, 30; 585/809, 515, 829, 811, 517, 832, 833, 852; 502/238

[56] References Cited

U.S. PATENT DOCUMENTS

| 2,272,301 | 2/1942 | Kinneberg et al. | 502/238 |
| 2,589,189 | 8/1949 | Ciapetta et al. | 585/671 |
| 3,403,109 | 9/1968 | Colgan et al. | 502/238 |
| 3,959,400 | 5/1976 | Lucki | 585/515 |
| 4,313,016 | 1/1982 | Manning | 585/515 |
| 4,356,339 | 10/1982 | Imaizumi et al. | 585/809 |
| 4,410,754 | 10/1983 | Gewartowski | 203/82 |
| 4,482,775 | 11/1984 | Smith, Jr. | 203/28 |

FOREIGN PATENT DOCUMENTS 0407864 12/1973 U.S.S.R. .............................. 585/671

OTHER PUBLICATIONS

Chem. Abstract, Yates et al., "Isomerization of n-Butenes over a Fluidized Silica-Alumina Catalyst", vol. 77, 1972, p. 102, No. 141849k.
Chem. Abstract, Chiyoda, "Silica-Alumina Porous Ceramics", vol. 101, 1984, p. 333, No. 96485q.
Chem. Abstract, Juguin et al., "High-Purity 1-Butene from a $C_4$ Olefin Cut", vol. 99, 1983, p. 155, No. 161209j.
Chem. Abstract, Choca et al., "Extruded Silica-Alumina Products for Catalyst Support", vol. 89, 1978, p. 420, No. 153425e.

Primary Examiner—S. Leon Bashore
Assistant Examiner—V. Manoharan
Attorney, Agent, or Firm—Jordan and Hamburg

[57] ABSTRACT

This invention provides a process for isolating and recovering butene-1 of high purity at high yield. Firstly, a butane-butene fraction containing 0.1 to 7 wt % of isobutylene, 10 to 50 wt % of butene-1 and 5 to 20 wt % of isobutane is rectified to reduce the content of isobutane to not more than 0.1 wt %. Then, the rectified butane-butene fraction is passed through a reactor packed with an extrusion molded silica-alumina catalyst to polymerize isobutylene at a reaction velocity as high as 50 times or more of that of butene-1, thus forming oligomers of isobutylene. Finally, the hydrocarbon mixture from the reactor is rectified to remove the oligomers of isobutylene and the other $C_4$-hydrocarbons.

11 Claims, 2 Drawing Figures

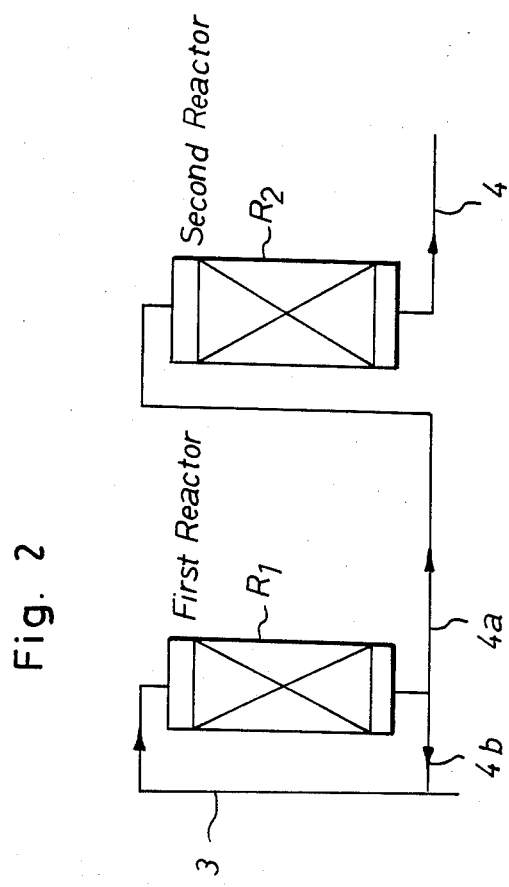

PROCESS FOR ISOLATING AND RECOVERING BUTENE-1 OF HIGH PURITY

BACKGROUND OF THE INVENTION

1. Field of the Invention

This invention relates to a process for isolating and recovering butene-1 of high purity at a high yield from a butane-butene fraction containing isobutylene and butene-1.

2. Prior Art

In order to isolate butene-1 from a butane-butene fraction containing isobutylene and butene-1, $C_4$-hydrocarbons other than butene-1 must be removed from the fraction by rectification. However, isobutylene cannot be removed by a simple distillation operation since the volatility of isobutylene resembles closely that of butene-1, in other words the difference in relative volatility between them is too small. For this reason, butene-1 of high purity could not be isolated through simple distillation or rectification process.

In order to isolate butene-1 of high purity from a butane-butene fraction containing isobutylene and butene-1, it is essential to remove isobutylene from the fraction substantially completely.

One of the known processes for removing isobutylene from the butane-butene fraction is the extraction process by the use of sulfuric acid. However, this known process requires a vast investment because an expensive material must be used for the facilities or apparatuses for effecting the process so that they withstand the corrosive action of sulfuric acid. Another known method of separating isobutylene is the absorption method by the use of zeolite. However, butene-1 cannot be satisfactorily separated from butene-2 by this known method.

In general, isobutylene is dimerized or polymerized by the use of an acidic catalyst. It has been proposed to remove the thus formed dimer and/or polymers from the butane-butene fraction by distillation. However, during this dimerization or polymerization reaction, butene-1 tends to be isomerized to be converted to butene-2. There is also a tendency that butene-1 is copolymerized with isobutylene to form co-oligomers.

It is, therefore, necessary to polymerize isobutylene while suppressing the undesired side reactions as little as possible in order to isolate and recover butene-1 at a high yield.

Silica-alumina, activated clay and strong acidic cation exchange resins have been known and used as catalysts for oligomerizing isobutylene. However, undesired side reactions of butene-1 cannot be suppressed completely by the use of these known catalysts.

OBJECTS AND SUMMARY OF THE INVENTION

A primary object of this invention is to provide a process for isolating and recovering butene-1 of high purity at a high yield.

Another object of this invention is to provide a process for isolating and recovering butene-1 of high purity from a butane-butene fraction containing isobutylene and butene-1, by which process isobutylene is removed substantially completely.

A further object of this invention is to provide a process for isolating and recovering butene-1 of high purity from a butane-butene fraction containing isobutylene and butene-1, wherein isobutylene is polymerized or oligomerized and the formed oligomers of isobutylene are removed without causing any undesired side reactions, such as isomerization of butene-1 or copolymerization of butene-1 and isobutylene.

The above and other objects of this invention will become apparent by referring to the following description.

According to this invention, there is provided a process for isolating and recovering butene-1 of high purity at a high yield, comprising the steps of:

subjecting a butane-butene fraction containing 0.1 to 7 wt% of isobutylene, 10 to 50 wt% of butene-1 and 5 to 20 wt% of isobutane to rectification to obtain a rectified butane-butene fraction having a reduced isobutane content of not more than 0.1 wt%;

continuously passing said rectified butane-butene fraction through a reactor packed with an extrusion molded silica-alumina catalyst at a temperature of from 0° C. to 100° C. and at a space velocity of liquid of from 0.1 to 100 $hr^{-1}$ under a pressure of from 1 to 50 atm. to polymerize isobutylene at a reaction velocity as high as 50 times or more of the reaction velocity of butene-1 to form oligomers of isobutylene in a hydrocarbon mixture, said extrusion molded silica-alumina catalyst having a surface area of 300 to 450 $m^2/g$, a pore volume per unit weight of 0.6 to 0.9 ml/g and an alumina content of 20 to 50 wt%; and rectifying the hydrocarbon mixture containing said oligomers and butane-butene to isolate butene-1 from the other $C_4$-hydrocarbons.

BRIEF DESCRIPTION OF THE DRAWING

FIG. 2 is a flow diagram showing another embodiment of reactors according to the process of this invention.

DESCRIPTION OF THE INVENTION

Figure 1:
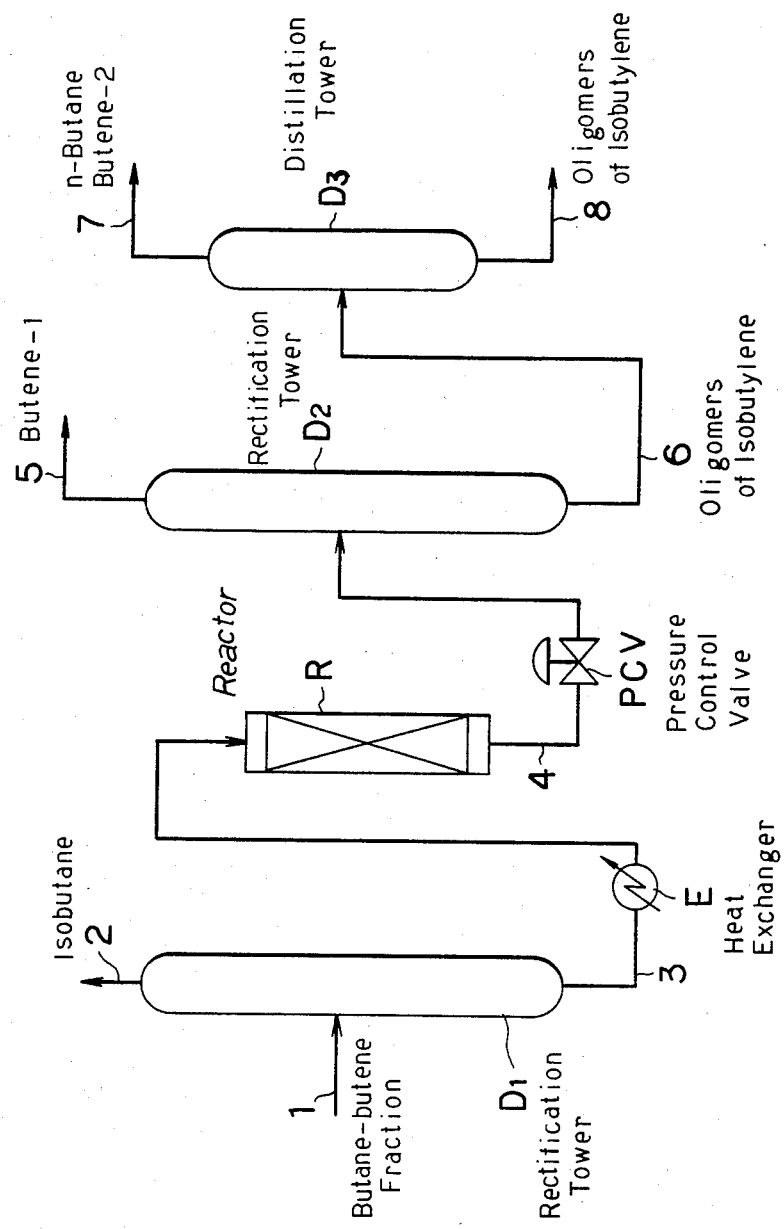
FIG. 1 appended to the specification is a flow diagram showing an embodiment of the process of this invention.

The present invention will now be described in detail hereinafter.

The starting material used in this invention is a butane-butene fraction containing 0.1 to 7 wt% of isobutylene, 10 to 50 wt% of butene-1 and 5 to 20 wt% of isobutane. Such a material may be available from $C_4$-fractions prepared by thermal cracking, steam cracking or catalytic cracking of petrolem. The starting material generally used in this invention is deprived of butadiene substantially completely, for instance to a content of less than 0.1 wt%.

In general, such a starting material contains butene-2, isobutane and n-butane, in addition to isobutylene and butene-1. A starting material containing more than 7 wt% of isobutylene cannot be effectively used. It is preferred that the content of isobutylene be within the range of 1 to 5 wt% and the content of butene-1 be within the range of 20 to 40 wt%.

One example of preferable butane-butene fraction used as the starting material in this invention is a mixture of unreacted $C_4$-hydrocarbons obtained at the step of the preparation of a liquid or semi-solid polymer by polymerizing a mixture of starting $C_4$-hydrocarbons in the presence of an aluminum chloride catalyst, said starting $C_4$-hydrocarbons being those obtained by cracking petroleum and from which butadiene is separated and removed. It has hitherto been known to prepare a liquid or semi-solid polymer (polybutene) by polymerizing isobutylene obtained in the mixture of C$_4$-hydrocarbons by subjecting the starting mixture of C$_4$-hydrocarbons deprived of butadiene to polymerization step in the presence of an aluminum chloride catalyst. Although the mixture of unreacted C$_4$-hydrocarbons after the polymerization reaction is reduced in content of isobutylene, it still contains about 1 to 7 wt%, generally 2 to 5 wt% of isobutylene. Butene-1 of high purity could not be obtained even if the mixture of unreacted C$_4$-hydrocarbons was directly subjected to distillation, and it is a common practice to consume the mixture as a fuel. In the process of this invention, such a mixture of unreacted C$_4$-hydrocarbons may be conveniently used as a preferable starting material.

Another example of the preferable butane-butene fraction used as the starting material in this invention is a mixture of unreacted C$_4$-hydrocarbons obtained at the step of the preparation of tert-butyl alcohol by reacting a mixture of starting C$_4$-hydrocarbons with water in the presence of an acidic catalyst, said starting C$_4$-hydrocarbons being those which are obtained by cracking petroleum and from which butadiene is separated and removed. It has hitherto been known to prepare tert-butyl alcohol from the C$_4$-hydrocarbon fraction deprived of butadiene by reacting the fraction with water in the presence of an acidic catalyst, such as sulfuric acid, hydrochloric acid or a sulfonic acid type cation exchange resin to hydrate isobutylene contained in the C$_4$-hydrocarbon fraction. The mixture of unreacted materials obtained by this known process contains generally 1 to 7 wt% of isobutylene, and has commonly consumed as a fuel. The aforementioned mixture of unreacted C$_4$-hydrocarbons may be advantageously used as a valuable starting material in the process of this invention.

In the process of this invention, it is essential to reduce the content of isobutane to not more than 0.1 wt% by the rectification of starting butane-butene fraction. Isobutane should be removed substantially completely prior to oligomerization of isobutylene for the reasons that isobutylene is oligomerized at a higher reaction velocity when the reaction mixture contains substantially no isobutane, as compared with the oligomerization reaction velocity where the reaction mixture contains isobutane, and that the reaction velocity of isobutylene becomes as high as 50 times or more of the reaction velocity of butene-1 in the absence of isobutane to increase the selectivity of butene-1. The selectivity of butene-1 as herein used is defined as follows. Let the first-order reaction velocity constant of isobutylene be $k_{i-c'4}$ and the first-order reaction velocity constant of butene-1 be $k_{c'4-1}$, the selectivity R is represented by the following equation of:

$$R = \frac{k_{i-c'4}}{k_{c'4-1}}.$$

Accordingly, the selectivity R takes a value of 50 or more in the practice of the process of the invention.

A portion of isobutylene is removed together with isobutane at the step of rectifying the butane-butene fraction for the removal of isobutane. As a result, the amount of isobutylene to be processed at the subsequent step of oligomerizing isobutylene is decreased when the butane-butene fraction is initially subjected to rectification for the removal of isobutane to provide another advantage that the life of the catalyst used in the step of oligomerizing isobutylene is prolonged. The content of isobutane should be reduced to a content of not more than 0.1 wt% by the rectification step carried out before the step of oligomerizing isobutylene, since the residing isobutane is concentrated at the final rectification step carried out after the step of oligomerizing isobutylene so that the content of isobutane in the product butene-1 is increased in the order of about 0.4 wt% or more if the effluent from the first rectification step contains more than 0.1 wt% of isobutane.

In the process of the invention, isobutylene contained in the starting butane-butene fraction is oligomerized in the presence of an extrusion molded silica-alumina catalyst which has a surface area of 300 to 450 m$^2$/g, a pore volume per unit weight of 0.6 to 0.9 ml/g and an alumina content of 20 to 50 wt%.

The silica-alumina catalyst used in the present invention is prepared by extruding a silica-alumina material synthesized by the conventional method. It is desirous that the silica-alumina material subjected to extrusion molding is in the form of paste. Materials of powder form may be used by adding with an appropriate quantity of water, alumina gel and silica gel to form pastes. After the extrusion molding step, the molded product is baked at a desired temperature of higher than 400° C. in an air or stream atmosphere. It is considered that the extrusion molded catalyst used in the present invention is decreased in resistance to dispersion of isobutylene entering into fine pores of the catalyst particles, when compared with the conventional catalyst prepared by compression molding, whereby the reaction activity of isobutylene is increased to facilitate selective oligomerization of isobutylene. The selectivity R to oligomerization of isobutylene of the coventional compression molded silica-alumina catalyst is about 20 to 30. In contrast thereto, we have found that the reaction activity of isobutylene is increased to raise the selectivity R by the use of the extrusion molded alumina-silica catalyst, the selectivity R being 50 or more even after the conversion rate of isobutylene reaches closely 100%.

Since the oligomerization reaction of isobutylene is an exothermic reaction, a temperature difference is created between the inlet and the outlet of the reactor packed with the aforementioned alumina-silica catalyst as the butane-butene fraction is passed therethrough. Particularly, when the content of isobutylene in the butane-butene fraction is high, the temperature at the vicinity of the outlet of the reactor is raised considerably. As the content of unreacted butene-1 may possibly be decreased with the temperature rise, it is required to obviate such a disadvantageous temperature rise in the reactor. Although a reactor equipped with manifold cooling tubes might be used, a complicated operation is needed for exchanging the catalyst when such a type of reactor is used. Moreover, even when the catalyst bed is cooled by manifold cooling tubes, the catalyst bed is frequently heated to a high temperature locally to affect the reaction adversely. Accordingly, when a reactor having no special cooling means is used, a one stage-one pass processing is preferred only when the content of isobutylene in the supplied butane-butene fraction is in the range of 0.1 to 2 wt%. If the butane-butene fraction containing 2 to 7 wt% of isobutylene is used, it is recommended to use a reactor provided with special cooling means or to divide the reactor into two stages so that the effluent from the first reactor is divided into two flows one of which is fed to the subsequent second reactor and the other of which, that is, the remainder of the effluent from the first reactor, is directly recirculated to the first reactor packed with the aforementioned silica-alumina catalyst. The amount of the divided flow recirculated to the first reactor is generally 1 to 15 times by weight, preferably 3 to 7, as large as that passed to the second reactor. The flow delivered to the second reactor is treated through a conventional one pass process. The temperature distribution in the first reactor may be controlled satisfactorily uniformly when an appropriate part of the effluent therefrom is recirculated. However, upon comparing the one stage recirculation process operated in the recyclic fashion with a one pass process, the so-called piston flow process, the reactivity of isobutylene in the former process is decreased to lower the yield of oligomers thereof and to increase the residing amount of unreacted isobutylene in the reaction mixture. In order to increase the reactivity of isobutylene, parameters for reaction must be brought to more severe conditions, for example, the reaction temperature is raised or the space velocity of liquid is lowered. However, under such severe conditions, the loss of butene-1 due to isomerization or polymerization increases, leading to decrease in butene-1 residing in the product. It is, thus, preferred that the material flow is processed through a first stage wherein the fresh make-up flow is mixed with the recirculated flow and wherein oligomerization of isobutylene is controlled to a relatively low level, for example the conversion rate of isobutylene to oligomers thereof being controlled to about 70 to 90%, and then the effluent from the first stage reactor is fed to the second stage reactor to react isobutylene residing in the effluent from the first stage reactor. The second stage reactor is operated in one pass fashion in order to suppress the reaction of butene-1 as little as possible, since the content of isobutylene in the flow delivered thereto is relatively low so that accumulation of reaction heat therein and the temperature difference between the inlet and outlet thereof are small.

The reaction temperature at the step of oligomerizing isobutylene ranges within 0° to 100° C. When two-stage process is adopted, the reaction temperature in both of the first and second reactors is 0° to 100° C., preferably 20° to 70° C. If the reaction temperature in either of the reactors is lower than 0° C., the reaction velocity is reduced so low as to result in unsatisfactory removal of isobutylene. On the other hand, as the reaction temperature in either of the reactors becomes higher than 100° C., participation in reaction of butene-1 is accelerated, resulting in increase of the loss of butene-1.

In the step of oligomerizing isobutylene, the reaction pressure in each reactor is 1 to 50 atm., preferably 5 to 30 atm., irrespective of whether the one-stage process or the two-stage process is adopted. If the reaction pressure in the reactor is lower than 1 atm., the reaction in the reaction system is carried out in a vapor phase so that the desired reaction cannot take place satisfactorily. On the contrary, a reaction pressure of higher than 50 atm. is disadvantageous from the industrial standpoint of view, because the reactors and the attachment should be pressure-proof in order to withstand such a high pressure.

The butane-butene fraction containing isobutylene and butene-1 is supplied from the top or bottom, preferably from the top, of the fixed catalyst bed continuously. The feed rate is controlled such that the space velocity of liquid flowing through the catalyst bed ranges within 0.1 to 100 $hr^{-1}$, preferably 1 to 50 $hr^{-1}$ (kg/kg×1/hr=$hr^{-1}$). The term "space velocity of liquid" as used throughout the specification and claims means the weight (in kg unit) of the flow supplied into the reactor per hour per 1 kg of the catalyst while excluding the weight of the recirculated flow for the first reactor, and as for the second reactor the same term means the weight (in kg unit) of the flow passing through the reactor per hour per 1 kg of the catalyst. If the space velocity of the supplied butane-butene fraction is less than 0.1 $hr^{-1}$, the yield of butane-butene fraction after being deprived of isobutylene is lowered to diminish the industrial value of the process. On the contrary, if the space velocity of the supplied fraction is more than 100 $hr^{-1}$, isobutylene is not removed sufficiently.

In the process of the invention, the effluent from the step of oligomerizing isobutylene is subjected to rectification to remove n-butane, butene-2 and oligomers of isobutylene from the bottom and product high purity butene-1 is isolated and recovered from the top of the rectification tower. In this final rectification step, a distillation tower having 50 to 100 plates or trays may be used. If it is desired to isolate and remove only the oligomers from the effluent from the bottom of the tower, another distillation tower having 3 to 40 plates or trays may be used for such a purpose.

In accordance with the process of the invention, the purity of the product butene-1 can be raised to higher than 99%, or further improved to higher than 99.5%. The aforementioned reaction conditions may be changed to more moderate conditions, or the conditions for each of the distillation operations may be changed to more moderate conditions when the required purity of the product is not so high.

According to the process of the invention, the yield of butene-1 recovered thereby is so good that the recovery rate (or remaining ratio thereof in the product) of butene-1 based on the quantity of butene-1 contained in the starting material is higher than 90% or 95% or even higher.

An embodiment of the process according to the present invention will now be described by referring to the flow diagram shown in the appended drawing.

Referring to FIG. 1, a feed butane-butene fraction is introduced through a conduit 1 to a rectification tower $D_1$. From the top of the tower $D_1$, isobutane and small amounts of isobutylene and butene-1 are removed. The rectified butane-butene fraction reduced in isobutane content to not more than 0.1 wt% is passed through a conduit 3 and maintained at a predetermined temperature by a heat exchanger E, and introduced into a reactor R having a fixed bed packed with an extrusion molded silica-alumina catalyst. The pressure in the reactor R is controlled by a pressure control valve PCV to a predetermined pressure. The pressure of the effluent from the reactor R is reduced through the valve PCV, and the effluent flow is passed through a conduit 4 to another rectification tower $D_2$. Referring to FIG. 2, the reactor R consists of a first reactor $R_1$ and a second reactor $R_2$. One part of the effluent from the first reactor $R_1$ is fed to the second reactor $R_2$ through a conduit 4a, whereas the other part of the effluent from the first reactor $R_1$ is recirculated through a conduit 4b to the first reactor $R_1$. The effluent flow from the second reactor $R_2$ is passed through a conduit 4 to the rectification tower $D_2$. High purity butene-1 is discharged from the top of the tower $D_2$ to be passed through a conduit 5, and the other residual $C_4$-hydrocarbons including oligomers of isobutylene are removed from the bottom of the tower $D_2$. The discharged flow from the bottom of the tower $D_2$ may be passed through a conduit 6 to a distillation tower $D_3$ where $C_4$-hydrocarbons including n-butane and butene-2 are separated from the top through a conduit 7 and oligomers of isobutylene are removed from the bottom and discharged through a conduit 8.

EXAMPLES OF THE INVENTION

The features of this invention will be described in detail with reference to examples. Incidentally, "%" stands for "% by weight" unless otherwise specified.

EXAMPLE 1

A silica-alumina catalyst was prepared by the coprecipitation method described below.

A diluted water glass solution containing 5% of $SiO_2$ was prepared by adding water to a water glass solution containing 29% of $SiO_2$. 400 g of the diluted water glass solution was added with concentrated sulfuric acid to obtain a silica hydrogel having a pH value of about 9, to which 360 g of an aqueous solution of aluminium sulfate (corresponding to a 6% $Al_2O_3$ solution) was added under vigorous agitation. A gel was formed by slightly heating for a few minutes. The gel was aged for one day, and then added with a 1% aqueous ammonia solution. The silica-alumina hydrogel was filtered, rinsed with an $NH_4NO_3$ solution, and then with distilled water. After drying at 120° C., the dried silica-alumina hydrogel was extrusion molded through an extruder and then baked at 550° C. in air.

The extrusion molded catalyst had a surface area of 380 $m^2/g$, a pore volume per unit weight of 0.75 ml/g and an alumina content of 29 wt%. 100 g of the catalyst was packed in a stainless steel reactor tube provided with an external heater. A butane-butene fraction containing 9.7% of isobutane, 2.4% of isobutylene and 31.2% of butene-1 was subjected to rectification to obtain a rectified $C_4$-fraction containing 2.4% of isobutylene and 32.8% of butene-1. The rectified $C_4$-fraction was passed through the reactor tube at a temperature of 30° C., under a pressure of 20 $kg/cm^2$ and at a WHSV of 14. The isobutylene content of the effluent was 0.079%, and the recovery rate of butene-1 was 95.0% (R=66.3). The effluent was rectified to obtain butene-1 having a purity of 99.8% from the top of the rectification tower.

EXAMPLE 2

Butadiene was removed from a by-product $C_4$-hydrocarbon mixture obtained by cracking naphtha. The residual $C_4$-hydrocarbon mixture deprived of butadiene was subjected to polymerization, using an aluminium chloride catalyst, and the unreacted $C_4$-hydrocarbon mixture was rectified to remove isobutane, whereby a $C_4$-fraction containing 4.3% of isobutylene, 29.7% of butene-1 and 0.05% of isobutane was obtained. The $C_4$-fraction was passed through the same reactor tube packed with the extrusion molded catalyst (Surface Area: 320 $m^2/g$, Pore Volume per unit Weight: 0.85 ml/g, Alumina Content: 30 wt%) as prepared in Example 1, at a temperature of 43° C., under a pressure of 30 $kg/cm^2$ and at a WHSV of 39. The content of isobutylene in the effluent from the reactor tube was 0.082%, and the recovery rate of butene-1 was 92.8% (R=53.0). The effluent was rectified to obtain butene-1 having a purity of 99.7% from the top of the rectification tower.

EXAMPLE 3

The residual $C_4$-hydrocarbon mixture deprived of butadiene as used in Example 2 was reacted with water in the presence of a sulfonic acid type cation exchange resin (available from Rohm & Haas Co. under the Trade Name of "Amberlyst-15"), and the product tert-butyl alcohol was removed to obtain an unreacted $C_4$-hydrocarbon mixture which was rectified to remove isobutane. The $C_4$-fraction deprived of isobutene contained 4.7% of isobutylene, 36.5% of butene-1 and 0.03% of isobutane. The $C_4$-fraction was passed through the same reactor tube packed with the catalyst as prepared in Example 1, at a temperature of 25° C., under a pressure of 15 $kg/cm^2$ and at a WHSV of 5.2. The effluent contained 0.082% of isobutylene, and the recovery rate of butene-1 was 95.2% (R=84.1). The effluent was rectified to obtain butene-1 having a purity of 99.6%.

Comparative Example 1

The same butane-butene fraction as used in Example 1 was processed similarly to Example 1 except that WHSV was changed to 7 and that a compression molded high alumina catalyst (Surface Area: 460 $m^2/g$, Pore Volume per Unit Weight: 0.7 ml/g, Alumina Content: 28 wt%) was used. The effluent from the reactor tube contained 0.37% of isobutylene, and the recovery rate of butene-1 was 88.0% (R=19.8).

In the foregoing description, the present invention has been specifically disclosed by referring to some examples thereof. However, it should be appreciated that various modifications and variations can be easily made by those skilled in the art without departing from the spirit of the invention. It is, thus, intended to include all such modifications and variations within the wide scope of the present invention defined by the appended claims.

What is claimed is:

1. A process for isolating and recovering butene-1 of high purity at a high yield, comprising the steps of:
    subjecting a butane-butene fraction containing 0.1 to 7 wt% of isobutylene, 10 to 50 wt% of butene-1 and 5 to 20 wt% of isobutane to rectification to obtain a rectified butane-butene fraction having a reduced isobutane content of not more than 0.1 wt%;
    continuously passing said rectified butane-butene fraction through a reactor packed with an extrusion molded silica-alumina catalyst at a temperature of from 0° C. to 100° C. and at a space velocity of liquid of from 0.1 to 100 $hr^{-1}$ under a pressure of from 1 to 50 atm. to polymerize isobutylene at a reaction velocity at least 50 times that of butene-1 to form oligomers of isobutylene in a hydrocarbon mixture, said extrusion molded silica-alumina catalyst having a surface area of 300 to 450 $m^2/g$, a pore volume per unit weight of 0.6 to 0.9 ml/g and an alumina content of 20 to 50 wt%; and
    rectifying the hydrocarbon mixture containing said oligomers and butane-butene to isolate butene-1 from the other $C_4$-hydrocarbons.

2. The process for isolating and recovering butene-1 according to claim 1, wherein said butane-butene fraction containing 0.1 to 7 wt% of isobutylene, 10 to 50 wt% of butene-1 and 5 to 20 wt% of isobutane is a mixture of unreacted C$_4$-hydrocarbons obtained at a step of preparing a liquid or semi-solid polymer by polymerizing a mixture of starting C$_4$-hydrocarbons in the presence of an aluminum chloride catalyst, said starting C$_4$-hydrocarbons being those which are obtained by cracking petroleum and from which butadiene is separated and removed.

3. The process for isolating and recovering butene-1 according to claim 1, wherein said butane-butene fraction containing 0.1 to 7 wt% of isobutylene, 10 to 50 wt% of butene-1 and 5 to 20 wt% of isobutane is a mixture of unreacted C$_4$-hydrocarbons obtained at a step of preparing tert-butyl alcohol by reacting a mixture of starting C$_4$-hydrocarbons with water in the presence of an acidic catalyst, said starting C$_4$-hydrocarbons being those which are obtained by cracking petroleum and from which butadiene is separated and removed.

4. The process for isolating and recovering butene-1 according to claim 1, wherein said extrusion molded silica-alumina catalyst is prepared from a silica-alumina paste.

5. The process for isolating and recovering butene-1 according to claim 4, wherein said silica-alumina paste is prepared by adding water to a silica-alumina powder.

6. The process for isolating and recovering butene-1 according to claim 4, wherein said extrusion molded silica-alumina catalyst is baked at a temperature of higher than 400° C. in air or steam.

7. The process for isolating and recovering butene-1 according to claim 1, wherein said rectified butane-butene fraction contains 2 to 7 wt% of isobutylene and wherein said reactor consists of first and second reactors and part of the effluent from the first reactor is fed to the second reactor whereas the remainder of the effluent from the first reactor is recirculated to the first reactor.

8. The process for isolating and recovering butene-1 according to claim 7, wherein said remainder of the effluent recirculated to said first reactor is 1 to 15 times by weight the amount passed to said second reactor.

9. The process for isolating and recovering butene-1 according to claim 8, wherein said remainder of the effluent recirculated to said first reactor is 3 to 7 times by weight the amount passed to said second reactor.

10. The process for isolating and recovering butene-1 according to claim 7, wherein the conversion rate of isobutylene to oligomers thereof in said first reactor is controlled to 70 to 90 wt%, the unreacted isobutylene being oligomerized in said second reactor.

11. The process for isolating and recovering butene-1 according to claim 10, wherein said second reactor is operated in one pass fashion.

* * * * *